United States Patent
Awad

(10) Patent No.: US 9,989,508 B2
(45) Date of Patent: Jun. 5, 2018

(54) SCANNING SYSTEM FOR TRACE DETECTION

(71) Applicant: VOTI INC., Dorval (CA)

(72) Inventor: William Awad, Ile Bizard (CA)

(73) Assignee: VOTI INC. (CA)

( * ) Notice: Subject to any disclaimer, the term of this patent is extended or adjusted under 35 U.S.C. 154(b) by 209 days.

(21) Appl. No.: 15/035,109

(22) PCT Filed: Nov. 7, 2014

(86) PCT No.: PCT/CA2014/051074
§ 371 (c)(1),
(2) Date: May 6, 2016

(87) PCT Pub. No.: WO2015/066813
PCT Pub. Date: May 14, 2015

(65) Prior Publication Data
US 2016/0282319 A1    Sep. 29, 2016

Related U.S. Application Data

(60) Provisional application No. 61/901,825, filed on Nov. 8, 2013.

(51) Int. Cl.
*G01N 1/02* (2006.01)
*G01N 33/00* (2006.01)

(52) U.S. Cl.
CPC ........... *G01N 33/0057* (2013.01); *G01N 1/02* (2013.01); *G01N 2001/024* (2013.01); *G01N 2001/028* (2013.01)

(58) Field of Classification Search
CPC ....... G01N 2001/024; G01N 2001/028; G01N 23/083
See application file for complete search history.

(56) References Cited

U.S. PATENT DOCUMENTS 4,020,346 A    4/1977 Dennis
6,304,629 B1   10/2001 Conway et al.
(Continued)

FOREIGN PATENT DOCUMENTS

JP    3946612 B2    7/2007

OTHER PUBLICATIONS

International Search Report for corresponding International Patent Application No. PCT/CA2014/051074 dated Jan. 20, 2015.

*Primary Examiner* — Tony Ko
(74) *Attorney, Agent, or Firm* — Hartman Global IP Law; Gary M. Hartman; Domenica N. S. Hartman

(57) ABSTRACT

A scanning system is for trace detection. The scanning system includes a main body enclosing a scanning chamber, the main body including a chamber inlet; a transport system configured to move an article through the scanning chamber along a scanning path; and a door mechanism provided along the scanning path. The door mechanism includes: a door frame mounted about the scanning path; at least one door panel movable relative to the door frame and being made of a radiation-shielding material; and a trace detector integrated into the at least one door panel. A method for trace involves using trace detectors integrated into the door mechanism for trace detection while the object is moving along a scanning path passing through a scanning chamber of a scanning system.

20 Claims, 9 Drawing Sheets

(56) References Cited

U.S. PATENT DOCUMENTS

| | | |
|---|---|---|
| 6,590,956 B2 | 7/2003 | Fenkart et al. |
| 7,062,011 B1 | 6/2006 | Tybinkowski et al. |
| 7,384,194 B2 * | 6/2008 | Gatten ................. G01N 23/046 378/20 |
| 7,636,418 B2 | 12/2009 | Anwar et al. |
| 7,706,507 B2 | 4/2010 | Williamson et al. |
| D658,294 S | 4/2012 | Awad |
| 2003/0085348 A1 | 5/2003 | Megerle |
| 2007/0133742 A1 | 6/2007 | Gatten |
| 2008/0025470 A1 | 1/2008 | Streyl |
| 2013/0114788 A1 | 5/2013 | Crass |
| 2013/0336447 A1 | 12/2013 | Morton |

\* cited by examiner

SCANNING SYSTEM FOR TRACE DETECTION

This application is a National Stage Application of PCT/CA2014/051074, filed 7 Nov. 2014, which claims benefit of U.S. Provisional Patent Application Ser. No. 61/901,825, filed 8 Nov. 2013 and which applications are incorporated herein by reference. To the extent appropriate, a claim of priority is made to each of the above disclosed applications.

FIELD

The present invention relates to trace detection in scanning systems. More particularly, the present invention relates to a scanning system comprising a door mechanism with trace detectors integrated therein and to a method for scanning articles associated thereto.

BACKGROUND

Scanning machines are often used to scan objects for the purpose of inspecting the scanned objects. Known scanning machines, such as the one disclosed in U.S. Pat. No. 4,020,346, include a conveyor to lead an object to be inspected into a scanning chamber where the object is subjected to radiation. A lead curtain is provided at an entrance and at an exit of the scanning chamber to contain the radiation within the chamber while allowing the passage of the object when it is conveyed in or out of the chamber.

Known to the Applicant are United States patent applications having Publication Nos. 2007/0133742, 2008/0025470, 2013/0114788 and 2013/0336447. Also known to the Applicant is U.S. Pat. No. 7,706,507 and Japan Patent No. 3,946,612. Each of the mentioned patents and patent applications disclose systems for containing radiation within the scanning chamber while allowing the passage of an object when it is conveyed in or out of the chamber.

Moreover, a known process for the detection of explosive material involves manually taking a sample of fine particles from an object in order to subject the sample to a detection process. Typically such fine particles are collected with a cloth, which is then analyzed by an analyzing system which may include, for example, a heating chamber where the temperature is raised to gasify the particles containing explosive chemicals, from which the resulting gases are then analyzed with a spectrometer in order to detect the presence of such explosive chemicals.

However, the teachings of the aforementioned suffer from drawbacks. For example, the inspection of an object involves the separate processes of scanning the object and detecting explosives, which can be both complicated and time consuming. Preferably, these processes should be simplified in order to make the inspection of objects more efficient.

Hence, in light of the aforementioned, there is a need for an improved system which, by virtue of its design and components, would be able to overcome or at least minimize some of the drawbacks of the prior art.

SUMMARY

The object of the present invention is to provide a device which, by virtue of its design and components, satisfies some of the above-mentioned needs and is thus an improvement over other related door systems for scanning devices, known in the prior art.

In accordance with the present invention, the above mentioned object is achieved, as will be easily understood, by a scanning system comprising a door mechanism with trace detectors integrated therein, such as the one briefly described herein and such as the one exemplified in the accompanying drawings.

According to a first aspect of the invention, there is provided a scanning system comprising: a main body enclosing a scanning chamber, the main body comprising a chamber inlet; a transport system configured to move an article through the scanning chamber along a scanning path; and a door mechanism provided along the scanning path. The door mechanism comprises: a door frame mounted about the scanning path; at least one door panel movable relative to the door frame and being made of a radiation-shielding material; and a trace detector integrated into the at least one door panel.

In an embodiment, the at least one door panel is hingedly connected to the door frame.

In an embodiment, the trace detector is mounted on an edge of the at least one door panel.

In an embodiment, the trace detector is mounted inside the at least one door panel.

In an embodiment, the door mechanism is provided at the chamber inlet.

In an embodiment, the main body further comprises a chamber outlet, and the door mechanism is provided at the chamber outlet.

In an embodiment, the at least one door panel comprises three door panels.

In an embodiment, the three door panels comprise first, second and third door panels, the first and second door panels mounted near a lower portion of the door frame and configured to pivot sideways relative to the door frame, and the third door panel mounted near an upper portion of the door frame and configured to pivot upwardly relative to the door frame.

In an embodiment, the at least one door panel comprises a proximate edge proximate to the door frame and a distal edge opposite the proximate edge, and the sample collecting mechanism is mounted to the distal edge of the at least one door panel.

In an embodiment, the at least one door panel comprises an inner face facing the scanning chamber and an outer face opposite the inner face, and the sample collecting mechanism is mounted to one of the inner face or the outer face of the at least one door panel.

In an embodiment, the trace detector comprises a vacuum device.

In an embodiment, the trace detector comprises at least one of a static brush, a rotating brush, a static cloth, and a rotating cloth.

In an embodiment, the trace detector further comprises a channel device fluidly connecting the trace detector to a system configured to analyze a collected sample.

In an embodiment, the trace detector comprises an electromagnetic detector.

In an embodiment, the at least one door panel is movable between an open configuration wherein the at least one door panel is oriented outwardly relative to the door frame and a closed configuration wherein the at least one door panel is substantially aligned with the door frame.

In an embodiment, the door mechanism further comprises an actuating mechanism configured to move the at least one door panel.

In an embodiment, the scanning system further comprises a proximity sensor mounted proximate to the door mechanism and a controller in communication with the actuating mechanism and said proximity sensor, the controller configured to control a movement of the door panels to avoid a physical contact between the at least one door panel and the article.

In an embodiment, the proximity sensor is mounted in the door mechanism.

According to second aspect of the present invention, a method for trace detection is provided, the method comprising: moving an article towards a scanning chamber along a scanning path; opening a door panel to allow the article to enter the scanning chamber unobstructed; using a trace detector integrated into the door panel in order to generate a signal indicative of a presence of a substance in the article, while the article passes into the scanning chamber; analyzing the signal generated by the trace detector; and closing the door panel in order to block radiation from exiting the scanning chamber.

In an embodiment the method further comprises detecting a proximity of the article relative to the door panel and moving the door panel to avoid contact with the article.

The objects, advantages and features of the present invention will become more apparent upon reading of the following non-restrictive description of preferred embodiments thereof, given for the purpose of exemplification only, with reference to the accompanying drawings.

DETAILED DESCRIPTION OF PREFERRED EMBODIMENTS

In the following description, the same numerical references refer to similar elements. The embodiments, geometrical configurations, materials mentioned and/or dimensions shown in the figures or described in the present description are preferred embodiments only, given for exemplification purposes only.

Moreover, although the preferred embodiment of the present invention as illustrated in the accompanying drawings comprises components such as two side door panels and an upper door panel, proximity sensors, etc., and although the preferred embodiment of the scanning system and corresponding parts thereof consists of certain geometrical configurations as explained and illustrated herein, not all of these components and geometries are essential to the invention and thus should not be taken in their restrictive sense, i.e. should not be taken as to limit the scope of the present invention. It is to be understood, as also apparent to a person skilled in the art, that other suitable components and cooperations thereinbetween, as well as other suitable geometrical configurations may be used for the scanning system according to the present invention, as will be briefly explained herein and as can be easily inferred herefrom, by a person skilled in the art, without departing from the scope of the invention.

Furthermore, the order of the steps of the method described herein should not be taken as to limit the scope of the invention, as the sequence of the steps may vary in a number of ways, without affecting the scope or working of the invention, as can also be understood.

Broadly described, in accordance with an embodiment, there is provided a sampling system for detecting traces of explosive chemicals or the like which are present on an object being inspected.

Figure 1A:
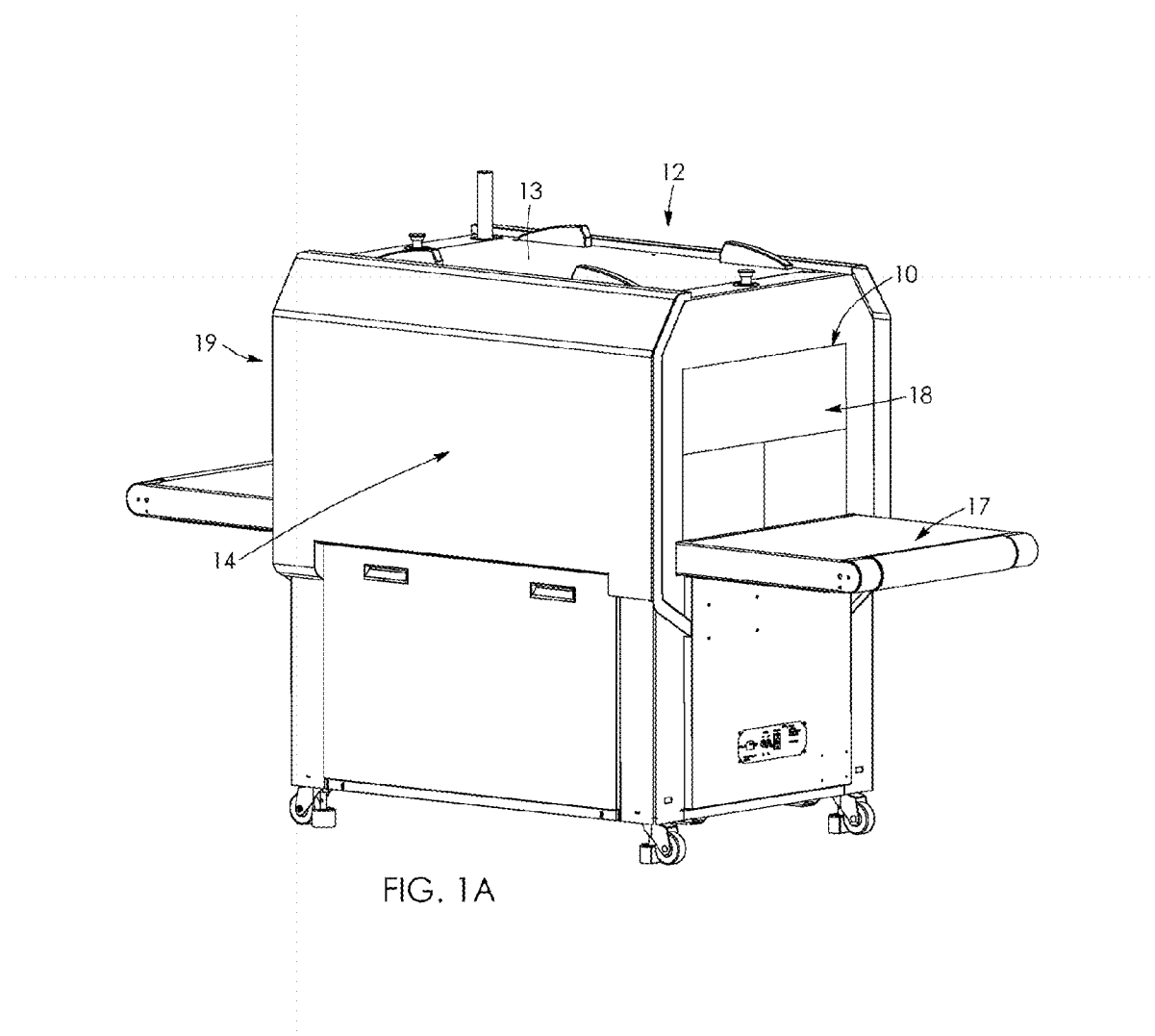
FIG. 1A is a right-side perspective view of a scanning device having a door panel mechanism in accordance with an embodiment of the present invention.
Figure 1B:
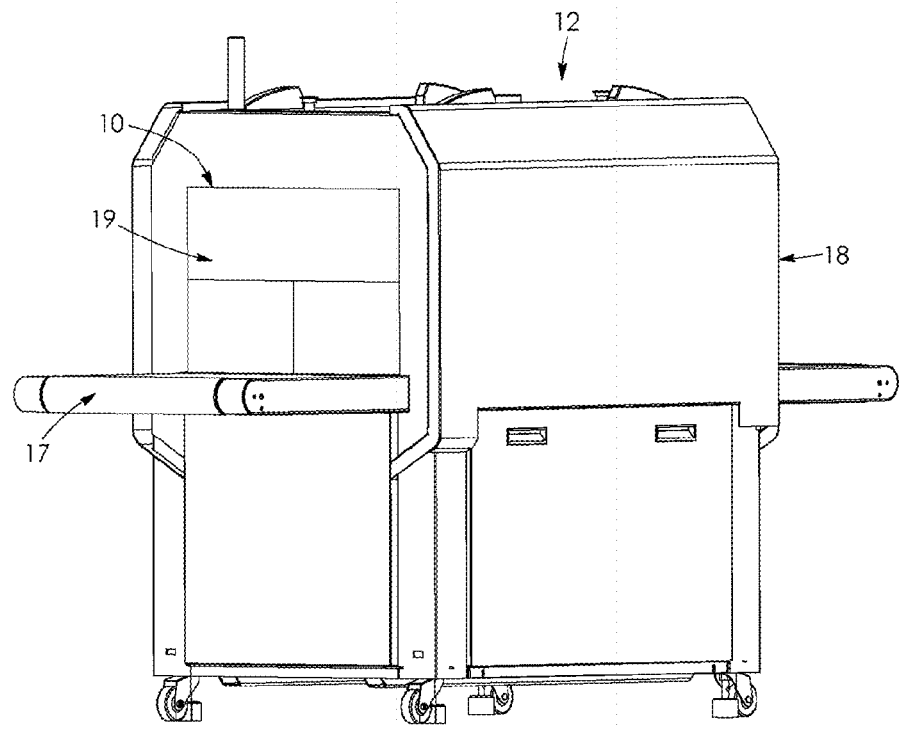
FIG. 1B is a left-side perspective view of the scanning device shown in FIG. 1A.
Figure 2:
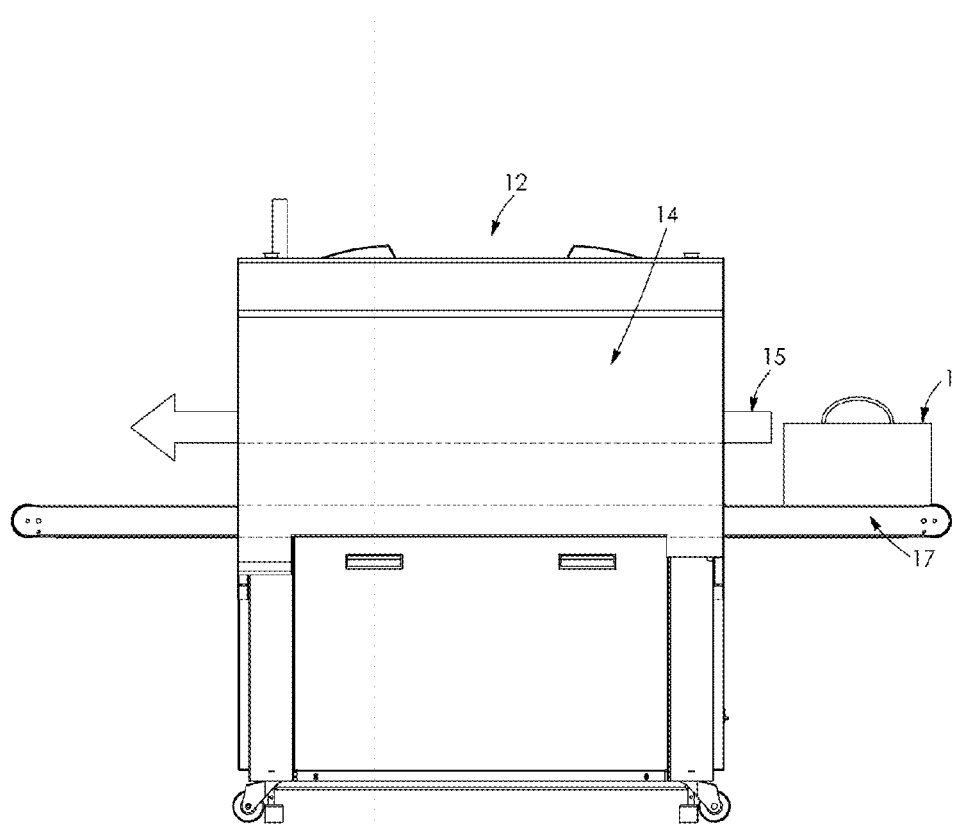
FIG. 2 is a side elevation view of the scanning device shown in FIG. 1A, schematically showing an article to be inspected and a scanning path through the scanning device.

With reference to FIGS. 1A and 1B, there is shown an embodiment of a scanning device 12 for trace detection according to a first aspect of the present invention. The scanning device 12 comprises a main body 13 enclosing a scanning chamber 14, a transport system 17, a chamber inlet 18 and outlet 19 on either side of the scanning chamber 14, and a door mechanism 10 provided at the inlet 18 and the outlet 19. With further reference to FIG. 2, the transport system 17 is configured to move and article 1 through the scanning chamber 14 along a scanning path 15.

In the illustrated embodiment, the transport system 17 is a conveyor belt. Of course, in other embodiments, other types of transport systems are possible, such as a sliding drawer for example. Additionally, in the illustrated embodiment, the chamber inlet 18 and the chamber outlet 19 are two separate passageways at opposite ends of the scanning device 12. Of course, in other embodiments, the scanning device can have a single passageway leading to the scanning chamber, the single passageway comprising both the chamber inlet 18 and outlet 19.

Figure 3:
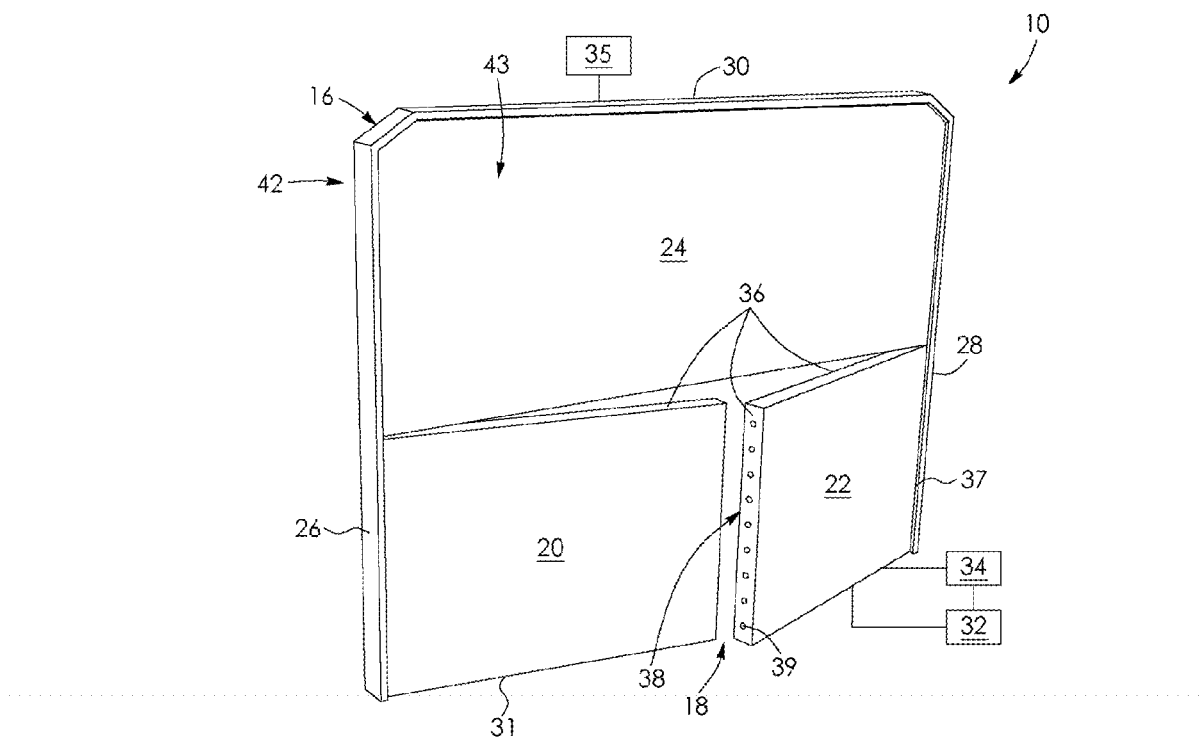
FIG. 3 is an enlarged view of the door system shown in FIG. 1A.

Referring to FIG. 3, a detailed view of the door mechanism 10 is shown. The door mechanism 10 comprises a door frame 16 mounted around the scanning path and defining the inlet or outlet communicating with the scanning chamber. The door mechanism further comprises door panels 20, 22, 24 mounted hingedly to the door frame 16. The door panels include two lower panels 20, 22 mounted to respective opposed sides 26, 28 of the door frame 16 so as to pivot sideways, and an upper panel 24 mounted to an upper portion 30 of the door frame 16 so as to pivot upwardly.

Of course, in alternate embodiments, the size, number, shape and configuration of the door panels can vary. For example, in a possible embodiment, the door mechanism 10 could comprise a single door panel. Additionally, in other possible embodiments, the door panels can be configured to move relative to the door frame in different possible ways. For example, the doors can be slidably mounted to the door frame and configured to slide in a direction substantially perpendicular to the scanning path.

Figure 4A:
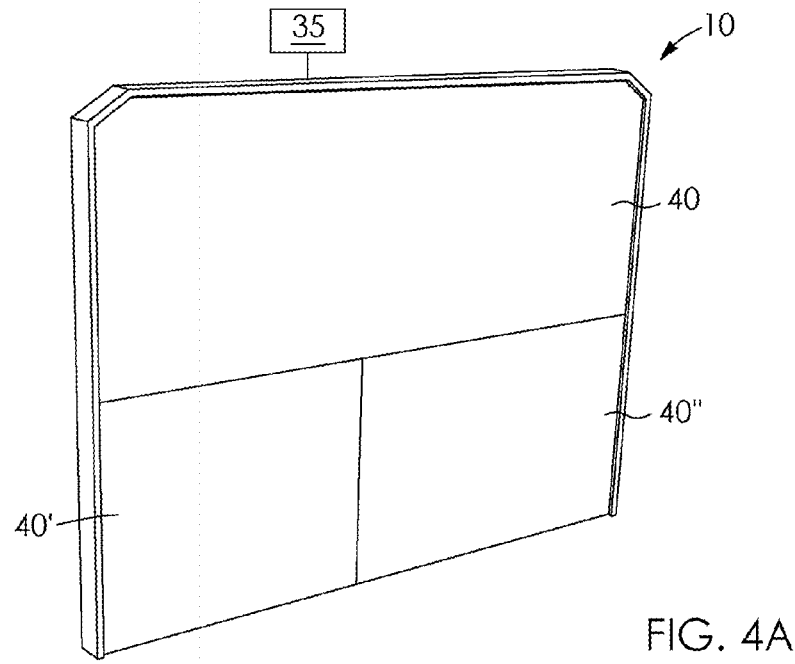
FIG. 4A is an enlarged view of the door system shown in FIG. 1A, showing the door panels in a closed configuration.
Figure 4B:
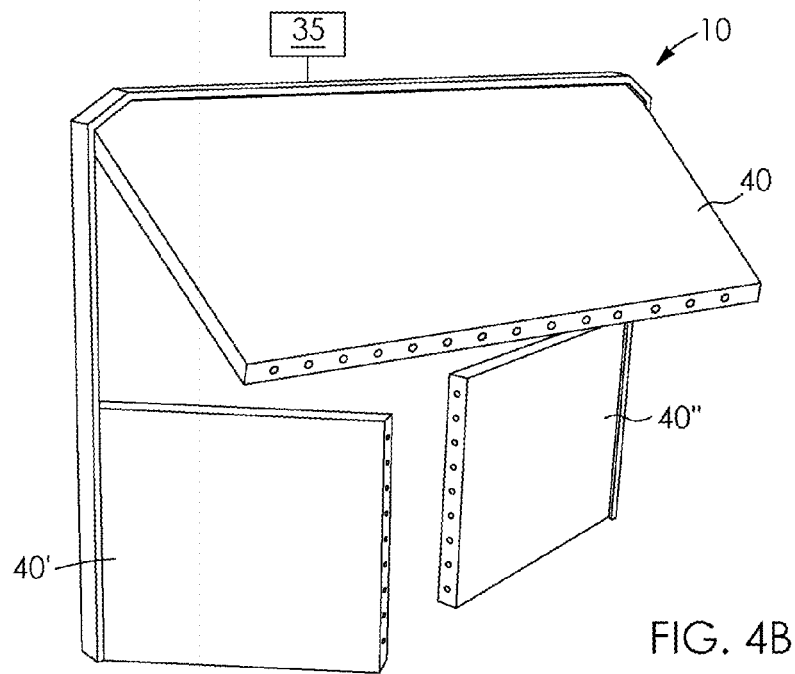
FIG. 4B is an enlarged view of the door system shown in FIG. 1A, showing the door panels in an open configuration.

With further reference to FIGS. 4A and 4B, each door panel 20, 22, 24 is operable between a closed configuration 40 and an open configuration 41. The door panels 20, 22, 24 may be actuated by an actuating mechanism 35. The actuating mechanism 35 can comprise, for example, a motor to rotate the doors, or a resilient biasing element to bias the doors towards the closed configuration 40.

In the closed configuration, the door panel (20, 22, 24) is oriented to block passage of radiation though the door frame 16. In the present embodiment, the door panel (20, 22, 24)

is substantially aligned with the door frame 16 in the closed configuration 40. In the open configuration, the door panel (20, 22, 24) is oriented to allow passage of an article through the door frame 16. In the present embodiment, the door panel (20, 22, 24) is oriented outwardly from the door frame 16 in the open configuration 41. In the present illustrations, the door panels open outward relative to the scanning chamber, but in other embodiments, the door panels can open inwardly relative to the scanning chamber.

Each door panel (20, 22, 24) comprises a shielding material to contain the radiation in the scanning chamber when the door panel (20, 22, 24) is oriented in the closed configuration 40. More particularly, each door panel (20, 22, 24) comprises an aluminum panel, lined with a lead material on each side. Of course, other types of shielding materials are also possible.

Moreover, as schematically represented in FIG. 3, sensors 32, such as proximity sensors for example, are mounted near or on the door panels (20, 22, 24), in order to sense a displacement of an object toward the door panels. A controller 34 is in communication between the sensors 32 and the actuating mechanism 35 in order to control the door panels (20, 22, 24) to operate between the open and closed configurations in accordance with the displacement of the object. More particularly, the controller 34 operates the door panels (20, 22, 24) to move open so as to avoid contact with the object but remain in close proximity thereto. Thus, the door mechanism 10 facilitates the passage of objects and further minimizes contact between the object and the scanning device 12 and therefore reduces contamination of particles between inspected objects.

It is to be understood that when smaller objects approach the door frame, only one or both of the lower side panels 20, 22 are operated by the controller 34 to open. In order to minimize radiation exposure outside the scanning chamber 14, the upper panel 24 is only operated to open when a taller object approaches the door frame 16.

Each door panel (20, 22, 24) comprises an inner face 42 facing the scanning chamber, and an outer face 43 opposite the inner face. Each door panel (20, 22, 24) also comprises trace detectors 39 mounted on edges 36 thereof. In the illustrated embodiment, the edges 36 comprise a proximate edge 37 proximate to the door frame 16, and a distal edge 38 opposite the proximate edge, the trace detectors 39 being mounted to the distal edge 38 of the door panel (20, 22, 24). Of course, the trace detectors 39 could be mounted to any of the edges 36, or to either of the inner face 42 or outer face 43. In other embodiments the trace detectors could be mounted inside the door panel (20, 22, 24). In the illustrated embodiment, the trace detectors 39 are mounted to the side edge of each of the door panels 20, 22, and 24. However, in other embodiments, the trace detectors 39 could be mounted to only some of the door panels.

The trace detectors 39 may include a plurality of collecting devices, such as rotating brushes for collecting a sample of particles from the object (which may include dust for example), along a plurality of surfaces, for example from three faces of the object (e.g. from opposing side faces and an upper face of the object). Alternatively, a collecting device may include a vacuum device in order to avoid contact with the object being inspected so as to reduce contamination between samples through multiple uses. In other embodiments, the trace detectors 39 can comprise an electromagnetic detector that can detect the presence of a substance in the article either actively, by emitting electromagnetic waves over the article and measuring the reflected waves, or passively by measuring the electromagnetic profile of the article being scanned. Some embodiments of the electromagnetic detector can include a spectrometer, among other systems, for example.

Figure 5:
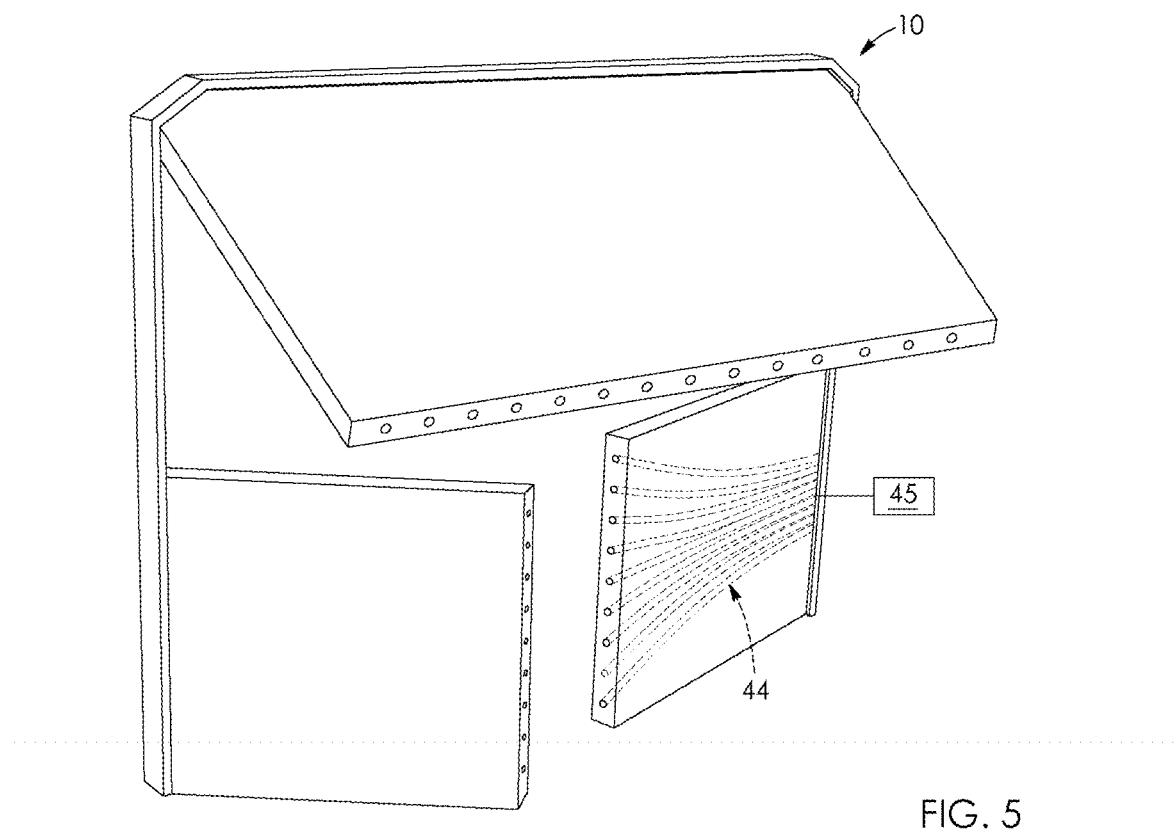
FIG. 5 is an enlarged view of the door system according to an alternate embodiment, schematically illustrating the channeling system.

Referring back to the above-described embodiment, the brushes are counter rotated to isolate the collected particles. As schematically represented in FIG. 5, a channeling mechanism 44 channels the collected sample to an analyzing system 45 which may include a heating chamber where particles of the sample are gasified, and subsequently analyzed for detection of chemical components. According to possible embodiments, the door mechanism 10 may comprise a cleaning mechanism to clean the brushes for a subsequent sampling.

It is to be understood that in particular embodiments, the heating chamber may be integrated with the collecting devices so as to directly collect the particles into the heating chamber. The analyzing system or any components thereof may be further incorporated with the scanning device. It is to be understood also that the analyzing system may be provided by any suitable device or series of devices to allow analyzing the collected sample for the purpose of detecting sought information on the content of the sample.

It is to be understood also that, although the present specification refers to the detection of explosives, it is to be understood that embodiments of the present description may also be suitable for sampling and detection of various other matter or components of which a detection of presence may be desired. It is to be understood also, that although the present specification refers to trace detection in the context of security inspections, the described embodiments or variants thereof may be readily used in many other contexts, for example for food inspection in food handling facilities, etc., or as another example, in healthcare facilities, etc.

It is to be understood also that, according to alternative embodiments, the sampling system may be provided in addition to the conventional lead-based curtain of scanning devices, in which case, the door panels may be designed more lightly as they would not require shield the radiation from inside the scanning chamber.

Figure 6A:
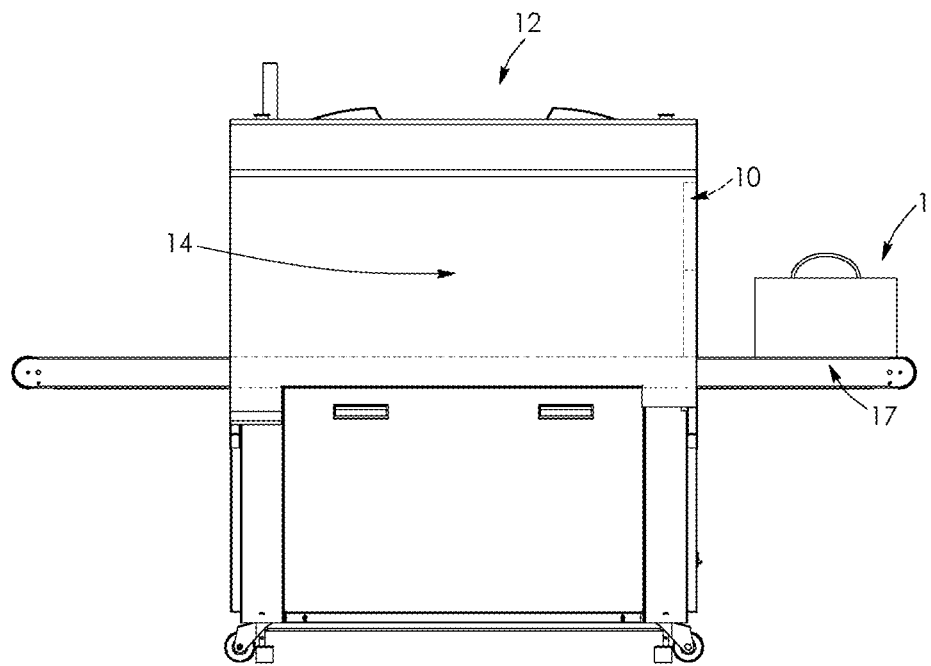
FIG. 6A, 6B and 6C are schematic representations of a method for scanning an article, according to an embodiment.
Figure 6B:
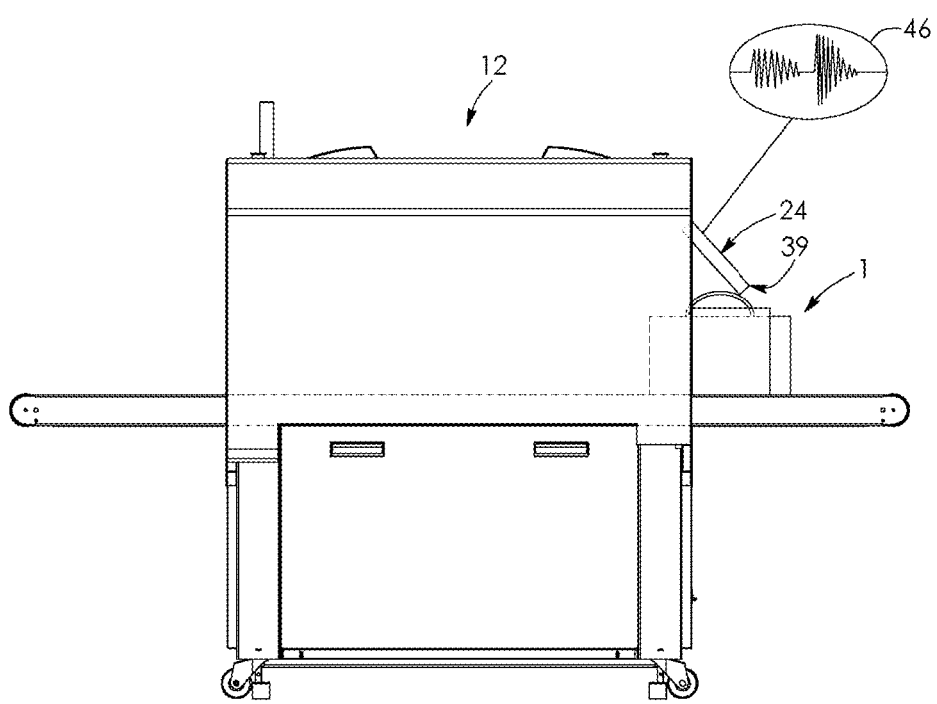
Figure 6C:
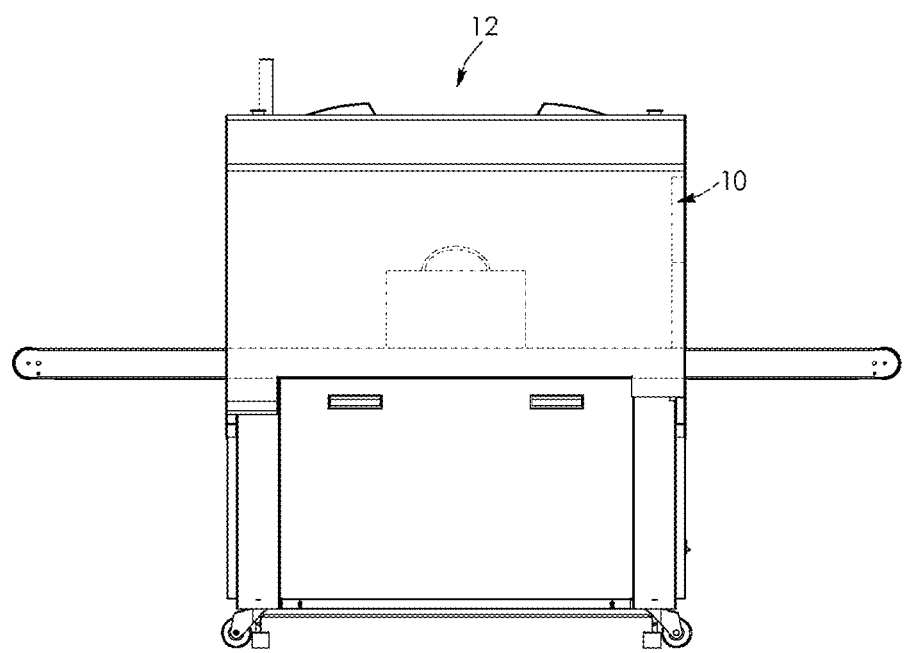

According to a second aspect of the present invention, and as illustrated in FIG. 6A-6C, there is provided a method for trace detection using a system such as the one described above. The method comprises moving an article 1 towards a scanning chamber 12 along a scanning path, opening a door panel 24 to allow the article to enter the scanning chamber 12 unobstructed, using a trace detector 39 integrated into the door panel in order to generate a signal 46 indicative of a presence of a substance in the article 1 while the article 1 passes into the scanning chamber 12, analyzing the signal generated by the trace detector and closing the door in order to block radiation from existing the scanning chamber.

The method may further comprise detecting proximity of the article relative to the door panel and moving the door panel to avoid contact with the article. According to possible embodiments, the opening of the door panels may be accomplished by an actuating mechanism. The door panels may be actuated to avoid contact with the article entirely, or to contact the surface of the article to gather sample particles, for example. In alternate embodiments, the door could be biased mechanically towards a closed position, and contact with the article could cause the doors to open towards the open position, allowing the article to pass through.

The above-described embodiments are considered in all respect only as illustrative and not restrictive, and the present application is intended to cover any adaptations or variations thereof, as apparent to a person skilled in the art.

Of course, numerous other modifications could be made to the above-described embodiments without departing from the scope of the invention, as apparent to a person skilled in the art.

The invention claimed is:

1. A scanning system comprising:
   a main body enclosing a scanning chamber, the main body comprising a chamber inlet;
   a transport system configured to move an article through the scanning chamber along a scanning path; and
   a door mechanism provided along the scanning path, the door mechanism comprising:
      a door frame mounted about the scanning path;
      at least one door panel movable relative to the door frame and being made of a radiation-shielding material; and
      a trace detector integrated into the at least one door panel.

2. A scanning system according to claim 1, wherein the at least one door panel is hingedly connected to the door frame.

3. A scanning system according to claim 1, wherein the trace detector is mounted on an edge of the at least one door panel.

4. A scanning system according to claim 1, wherein the trace detector is mounted inside the at least one door panel.

5. A scanning system according to claim 1, wherein the door mechanism is provided at the chamber inlet.

6. A scanning system according to claim 1, wherein the main body further comprises a chamber outlet, and wherein the door mechanism is provided at the chamber outlet.

7. A scanning system according to claim 1, wherein the at least one door panel comprises three door panels.

8. A scanning system according to claim 7, wherein the three door panels comprise first, second and third door panels, the first and second door panels mounted near a lower portion of the door frame and configured to pivot sideways relative to the door frame, and the third door panel mounted near an upper portion of the door frame and configured to pivot upwardly relative to the door frame.

9. A scanning system according to claim 1, wherein the at least one door panel comprises a proximate edge proximate to the door frame and a distal edge opposite the proximate edge, and wherein the sample collecting mechanism is mounted to the distal edge of the at least one door panel.

10. A scanning system according to claim 1, wherein the at least one door panel comprises an inner face facing the scanning chamber and an outer face opposite the inner face, and wherein the sample collecting mechanism is mounted to one of the inner face or the outer face of the at least one door panel.

11. A scanning system according to claim 1, wherein the trace detector comprises a vacuum device.

12. A scanning system according to claim 1, wherein the trace detector comprises at least one of a static brush, a rotating brush, a static cloth, and a rotating cloth.

13. A scanning system according to claim 1, wherein the trace detector further comprises a channel device fluidly connecting the trace detector to a system configured to analyze a collected sample.

14. A scanning system according to claim 1, wherein the trace detector comprises an electromagnetic detector.

15. A scanning system according to claim 1, wherein the at least one door panel is movable between an open configuration wherein the at least one door panel is oriented outwardly relative to the door frame and a closed configuration wherein the at least one door panel is substantially aligned with the door frame.

16. A scanning system according to claim 1, wherein the door mechanism further comprises an actuating mechanism configured to move the at least one door panel.

17. A scanning system according to claim 16 further comprising a proximity sensor mounted proximate to the door mechanism and a controller in communication with the actuating mechanism and said proximity sensor, the controller configured to control movement of the door panels to avoid physical contact between the at least one door panel and the article.

18. A scanning system according to claim 17, wherein the proximity sensor is mounted in the door mechanism.

19. A method for trace detection, the method comprising:
   a) moving an article towards a scanning chamber along a scanning path;
   b) opening a door panel to allow the article to enter the scanning chamber unobstructed;
   c) using a trace detector integrated into the door panel in order to generate a signal indicative of a presence of a substance in the article, while the article passes into the scanning chamber;
   d) analyzing the signal generated by the trace detector; and
   e) closing the door panel in order to block radiation from exiting the scanning chamber.

20. The method for trace detection according to claim 19, wherein step b) comprises detecting a proximity of the article relative to the door panel and moving the door panel to avoid contact with the article.

* * * * *